United States Patent
Fors et al.

(10) Patent No.: US 7,289,825 B2
(45) Date of Patent: *Oct. 30, 2007

(54) METHOD AND SYSTEM FOR UTILIZING WIRELESS VOICE TECHNOLOGY WITHIN A RADIOLOGY WORKFLOW

(75) Inventors: Steven Lawrence Fors, Chicago, IL (US); Khal A. Rai, Round Lake, IL (US); Mark M. Morita, Arlington Heights, IL (US)

(73) Assignee: General Electric Company, Schenectady, NY (US)

( * ) Notice: Subject to any disclaimer, the term of this patent is extended or adjusted under 35 U.S.C. 154(b) by 698 days.

This patent is subject to a terminal disclaimer.

(21) Appl. No.: 10/801,881

(22) Filed: Mar. 15, 2004

(65) Prior Publication Data

US 2005/0202843 A1    Sep. 15, 2005

(51) Int. Cl.
*H04M 1/00* (2006.01)
*G06Q 10/00* (2006.01)
*G06Q 50/00* (2006.01)
*G06F 15/16* (2006.01)
*H04R 25/00* (2006.01)

(52) U.S. Cl. .............................. 455/556.1; 340/572.1; 381/314; 705/2; 709/208

(58) Field of Classification Search ................ 395/500; 381/314; 340/572.1; 705/2; 455/556.1
See application file for complete search history.

(56) References Cited

U.S. PATENT DOCUMENTS

| 5,867,688 | A  | * | 2/1999  | Simmon et al. | ............ 709/208 |
| 6,718,043 | B1 | * | 4/2004  | Boesen        | ........................ 381/314 |
| 6,954,148 | B2 | * | 10/2005 | Pulkkinen et al. | ....... 340/572.1 |
| 2003/0050794 | A1 | * | 3/2003 | Keck         | ............................. 705/2 |
| 2005/0202843 | A1 | * | 9/2005 | Fors et al.  | ............... 455/556.1 |
| 2005/0202844 | A1 | * | 9/2005 | Jabri et al. | ............... 455/556.1 |

* cited by examiner

*Primary Examiner*—Willaim D. Cumming
(74) *Attorney, Agent, or Firm*—McAndrews, Held & Malloy, Ltd.; Peter J. Vogel; Michael A. Dellapenna

(57) ABSTRACT

Methods and systems for consolidating the workflow of various devices into a wireless, voice-enabled workflow. A method includes establishing a connection between a wireless, voice-enabled device and a data system using an interface and accessing the data system using voice commands via the connection between the wireless communication device and the data system. Voice commands may be used to facilitate data acquisition, data retrieval, order entry, dictation, audio playback, voice over IP conferencing, paging, and/or data analysis, for example. A plurality of connections may be established between the wireless, voice-enabled device and a plurality of data systems. WiFi wireless technology or other standard for voice and data transfer between devices without use of cables, for example, may be used to facilitate hands-free hygienic, centralized operation of a plurality of data systems using the wireless, voice-enabled device and the interface.

19 Claims, 4 Drawing Sheets

METHOD AND SYSTEM FOR UTILIZING WIRELESS VOICE TECHNOLOGY WITHIN A RADIOLOGY WORKFLOW

BACKGROUND OF THE INVENTION

The present invention generally relates to wireless speech communication in a clinical environment. In particular, the present invention relates to use of wireless voice technology to improve clinical workflow.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

In a healthcare or clinical environment, such as a hospital, a large number of employees and patients may result in confusion or delay when trying to reach other medical personnel for examination, treatment, consultation, or referral, for example. A delay in contacting other medical personnel may result in further injury or death to a patient. Additionally, a variety of distraction in a clinical environment may frequently interrupt medical personnel or interfere with their job performance. Furthermore, workspaces, such as a radiology workspace, may become cluttered with a variety of monitors, data input devices, data storage devices, and communication device, for example. Cluttered workspaces may result in efficient workflow and service to clients, which may impact a patient's health and safety or result in liability for a healthcare facility.

Data entry and access is also complicated in a typical healthcare facility. Speech transcription or dictation is typically accomplished by typing on a keyboard, dialing a transcription service, using a microphone, using a Dictaphone, or using digital speech recognition software at a personal computer. Such dictation methods involve a healthcare practitioner sitting in front of a computer or using a telephone, which may be impractical during operational situations. Similarly, for access to electronic mail or voice messages, a practitioner must typically use a computer or telephone in the facility. Access outside of the facility or away from a computer or telephone is limited.

Thus, management of multiple and disparate devices, positioned within an already crowded environment, that are used to perform daily tasks is difficult for medical or healthcare personnel. Additionally, a lack of interoperability between the devices increases delay and inconvenience associated with the use of multiple devices in a healthcare workflow. The use of multiple devices may also involve managing multiple logons within the same environment. A system and method for improving ease of use and interoperability between multiple devices in a healthcare environment would be highly desirable.

In a healthcare environment involving extensive interaction with a plurality of devices, such as keyboards, computer mousing devices, imaging probes, and surgical equipment, repetitive motion disorders often occur. A system and method that eliminates some of the repetitive motion in order to minimize repetitive motion injuries would be highly desirable.

Additionally, in a healthcare workflow, healthcare providers often consult or otherwise interact with each other. Such interaction typically involves paging or telephoning another practitioner. Thus, interaction between healthcare practitioners may be time-and energy-consuming. Therefore, there is a need for a system and method to simplify and improve communication and interaction between healthcare practitioners.

Healthcare environments, such as hospitals or clinics, include clinical information systems, such as hospital information systems (HIS) and radiology information systems (RIS), and storage systems, such as picture archiving and communication systems (PACS). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

In current information systems, such as PACS, information is entered or retrieved using a local computer terminal with a keyboard and/or mouse. During a medical procedure or at other times in a medical workflow, physical use of a keyboard, mouse or similar device may be impractical (e.g., in a different room) and/or unsanitary (i.e., a violation of the integrity of an individual's sterile field). Re-sterilizing after using a local computer terminal is often impractical for medical personnel in an operating room, for example, and may discourage medical personnel from accessing medical information systems. Thus, a system and method providing access to a medical information system without physical contact would be highly desirable to improve workflow and maintain a sterile field.

Imaging systems are complicated to configure and to operate. Often, healthcare personnel may be trying to obtain an image of a patient, reference or update patient records or diagnosis, and ordering additional tests or consultation. Thus, there is a need for a system and method that facilitate operation and interoperability of an imaging system and related devices by an operator.

In many situations, an operator of an imaging system may experience difficulty when scanning a patient or other object using an imaging system console. For example, using an imaging system, such as an ultrasound imaging system, for upper and lower extremity exams, compression exams, carotid exams, neo-natal head exams, and portable exams may be difficult with a typical system control console. An operator may not be able to physically reach both the console and a location to be scanned. Additionally, an operator may not be able to adjust a patient being scanned and operate the system at the console simultaneously. An operator may be unable to reach a telephone or a computer terminal to access information or order tests or consultation. Providing an additional operator or assistant to assist with examination may increase cost of the examination and may produce errors or unusable data due to miscommunication between the operator and the assistant. Thus, a method and system that facilitates operation of an imaging system and related services by an individual operator would be highly desirable.

Thus, there is a need for a system and method to improve clinical workflow using wireless communication technology.

BRIEF SUMMARY OF THE INVENTION

Certain embodiments of the present invention provide a method and system for improved clinical workflow using wireless communication. In an embodiment, the system includes a remote system in a healthcare facility that is used for executing an operation, storing data, and/or retrieving data. The system also includes a wireless communication device for voice control of the remote system in the healthcare facility. The wireless communication device allows centralized control of the remote system to facilitate executing an operation, storing data, and/or retrieving data. The system further includes an interface for relaying communication between the remote system and the wireless communication device. The interface displays and/or plays back data from the remote system. The system may further include a plurality of remote systems capable of communicating with the wireless communication device.

In an embodiment, the interface displays data from the wireless communication device. In an embodiment, the wireless communication device is a device communicating use a standard for voice and data transfer between devices without use of cables, such as BLUETOOTH®, a WiFi device, or other wireless communication device. The wireless communication device may be implemented as a wireless headset, for example. The wireless communication device may produce an audio response from the remote system. In an embodiment, the interface is integrated with the wireless communication device. Rather than pass through the interface, in an embodiment the wireless communication device may communicate directly with the remote system. The wireless communication device and the interface may control the remote system in order to perform data acquisition, data retrieval, order entry, dictation, audio playback, voice over IP conferencing, paging, and/or data analysis, for example.

In an embodiment, the method includes establishing a communication link between a wireless communication device and a remote system at a first location and utilizing voice commands to transmit data to, retrieve data from, and/or trigger functions at the remote system via the communication link. An interface may be used to establish the communication link between the wireless communication device and the remote system.

The method may also include receiving a response from the remote system. Additionally, a second communication link may be established between the wireless communication device and a second remote system at a second location. In an embodiment, a plurality of communication links may be established between the wireless communication device and a plurality of remote systems at the first location. Authentication may be performed when establishing a communication link. Voice commands may be used to perform at least one of data acquisition, data retrieval, order entry, dictation, audio playback, voice over IP conferencing, paging, and data analysis.

In another embodiment, a method for consolidating the workflow of various devices into a wireless, voice-enabled workflow includes establishing a connection between a wireless, voice-enabled device and a data system using an interface and accessing the data system using voice commands via the connection between the wireless communication device and the data system. Voice commands may be used to facilitate data acquisition, data retrieval, order entry, dictation, audio playback, voice over IP conferencing, paging, and/or data analysis, for example. In an embodiment, a plurality of connections may be established between the wireless, voice-enabled device and a plurality of data systems. BLUETOOTH® technology (e.g., use a standard for voice and data transfer between devices without use of cables) or WiFi wireless technology, for example, may be used to facilitate hands-free hygienic, centralized operation of a plurality of data systems using the wireless, voice-enabled device and the interface.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

The present invention relates to a wireless voice communication system and method for improving workflow in a medical environment, such as radiology workflow, examination workflow, administrative workflow, physician workflow, or other clinical workflow. For purposes of illustration, certain embodiments will be described below in relation to a radiology workflow.

Figure 1:
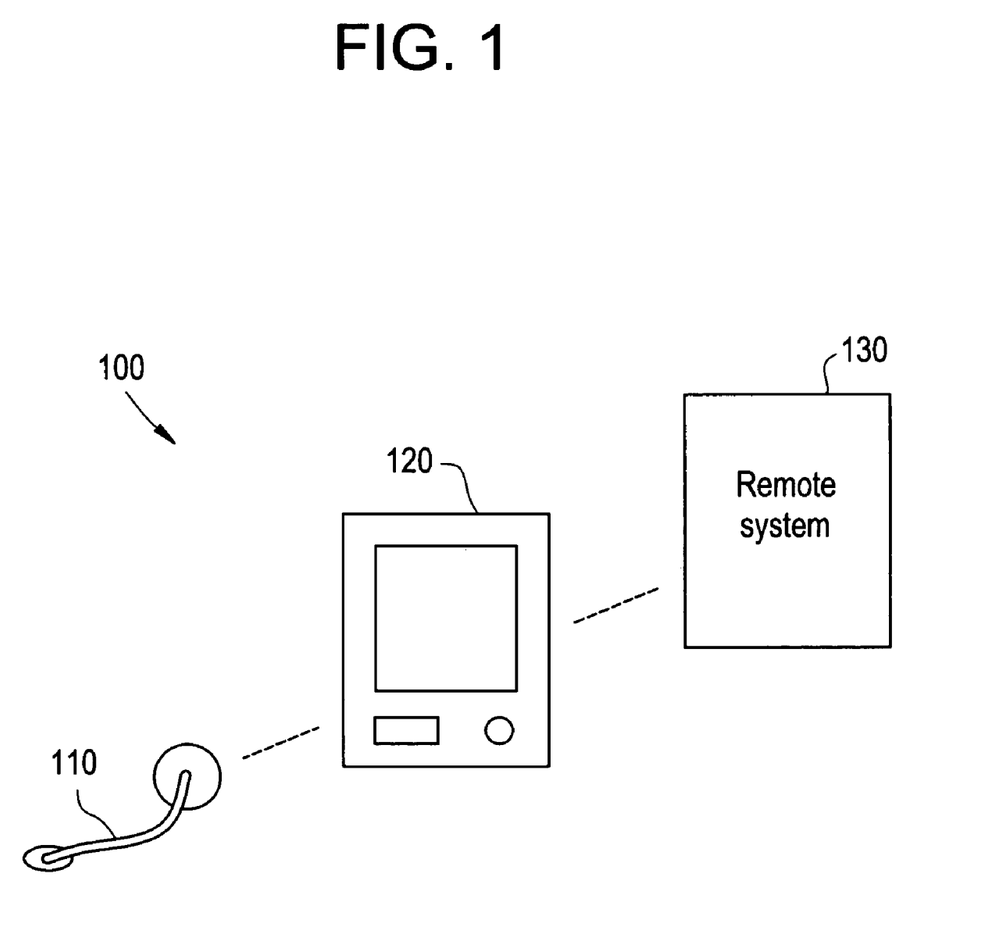
FIG. 1 illustrates a wireless voice communication system used in accordance with an embodiment of the present invention.

FIG. 1 illustrates a wireless voice communication system 100 used in accordance with an embodiment of the present invention. The system 100 includes a wireless communication device 110 and an interface 120. The communication device 110 and interface 120 allow a user to input and retrieve information from a remote system 130 and to execute functions at the remote system 130. The remote system 130 may be a personal computer, a workstation, a server, a picture archiving and communication system, an ECG system, a patient monitoring system, an imaging system, or other data storage or processing device, for example.

The interface 120 facilitates wireless communication and provides audio and video output, for example. The interface 120 may be a personal computer, a laptop computer, a tablet computer, a personal digital assistant, a handheld computer, a cellular phone, or other data processing device. The wireless communication device 110 is a wireless, voice-enabled communication device for transmitting spoken word commands, for example. The wireless communication device 110 may be a wireless headset, wireless microphone, wireless radio, or other wireless communication device, for example. An example of a wireless headset is a BLUETOOTH® technology (e.g., use a standard for voice and data transfer between devices without use of cables), WiFi, or 802.11g wireless headset. Alternatively, the communication device 110 may be an infrared communication device or may be connected by a wire to the interface 120.

In an embodiment, the interface 120 and the wireless communication device 110 may be integrated into a single unit (for example, a display screen integrated into a headset). In another embodiment, the interface 120 and/or the wireless communication device 110 may be worn by a user or are attachable to the user.

BLUETOOTH®, for example, is a standard for voice and data transfer over a wireless medium. BLUETOOTH® wireless technology enables a variety of devices to be connected without the use of cables and enhances connectivity and information exchange capabilities between devices on a wireless network. The BLUETOOTH® protocol uses a 2.4 GHz frequency band for wireless communication between electronic devices. Data is transmitted between devices via a short-range wireless 2.4 GHz connection rather than a physical cable connecting the devices. Devices may be synchronized to communicate with each other using BLUETOOTH® technology.

BLUETOOTH® technology includes multiple levels of data transfer protocols and data transfer functionality. BLUETOOTH® technology supports a variety of system-level profiles for data transfer, such as an audio/video remote control profile, a cordless telephony profile, an intercom profile, an audio/video distribution profile, a headset profile, a hands-free profile, a file transfer protocol, a file transfer profile, and/or an imaging profile. Hardware, such as the wireless communication device 110 and the interface 120, is used to support BLUETOOTH® wireless transmission in a personal area network (PAN) or other network.

Voice and speech recognition capability may be integrated with BLUETOOTH® or other wireless communication through software. For example, a computer with a wireless interface card running BLUETOOTH® or other voice and data transfer software and voice recognition software, such as Microsoft Windows XP® or a standalone voice recognition software, may facilitate verbal control of a system.

In an embodiment, the wireless communication device 110 is used to transmit commands and/or data to the remote system 130 via the interface 120. For example, an operator speaks, and the speech is received at the device 110. Alternatively, the communication device 110 may transmit directly to the remote system 130. Audio input from the wireless communication device 110 is transferred via asynchronous and/or synchronous layer communication. A BLUETOOTH® headset profile, for example, may employ asynchronous (ACL) and synchronous (SCO) layers from a generic audio distribution transport protocol to communicate between the interface 120 and the wireless device 110. The ACL layer may be used to manage on/off, volume, and device pairing data, for example, for operation of the communication system 100. The ACL layer has a bandwidth of 1 Mbps, for example, to accommodate higher quality voice or audio data. The SCO layer transmits voice data at a rate of, for example, 64 Kbps. The interface 120 interacts with the wireless communication device 110 and the remote system 130 and transmits audio data between the remote system 130 and the wireless device 110. The wireless communication device 110, the interface 120, and the remote system 130 may communicate up to a range of approximately 10 meters, for example.

In an embodiment, the wireless communication device 110 is used to transmit commands and/or data to the remote system 130 via the interface 120. For example, an operator speaks, and the speech is received at the device 110. Alternatively, the communication device 110 may transmit directly to the remote system 130. Audio input from the wireless communication device 110 is transferred via asynchronous and/or synchronous layer communication. A Bluetooth headset profile, for example, may employ asynchronous (ACL) and synchronous (SCO) layers from a generic audio distribution transport protocol to communicate between the interface 120 and the wireless device 110. The ACL layer may be used to manage on/off, volume, and device pairing data, for example, for operation of the communication system 100. The ACL layer has a bandwidth of 1 Mbps, for example, to accommodate higher quality voice or audio data. The SCO layer transmits voice data at a rate of, for example, 64 Kbps. The interface 120 interacts with the wireless communication device 110 and the remote system 130 and transmits audio data between the remote system 130 and the wireless device 110. The wireless communication device 110, the interface 120, and the remote system 130 may communicate up to a range of approximately 10 meters, for example.

Figure 2:
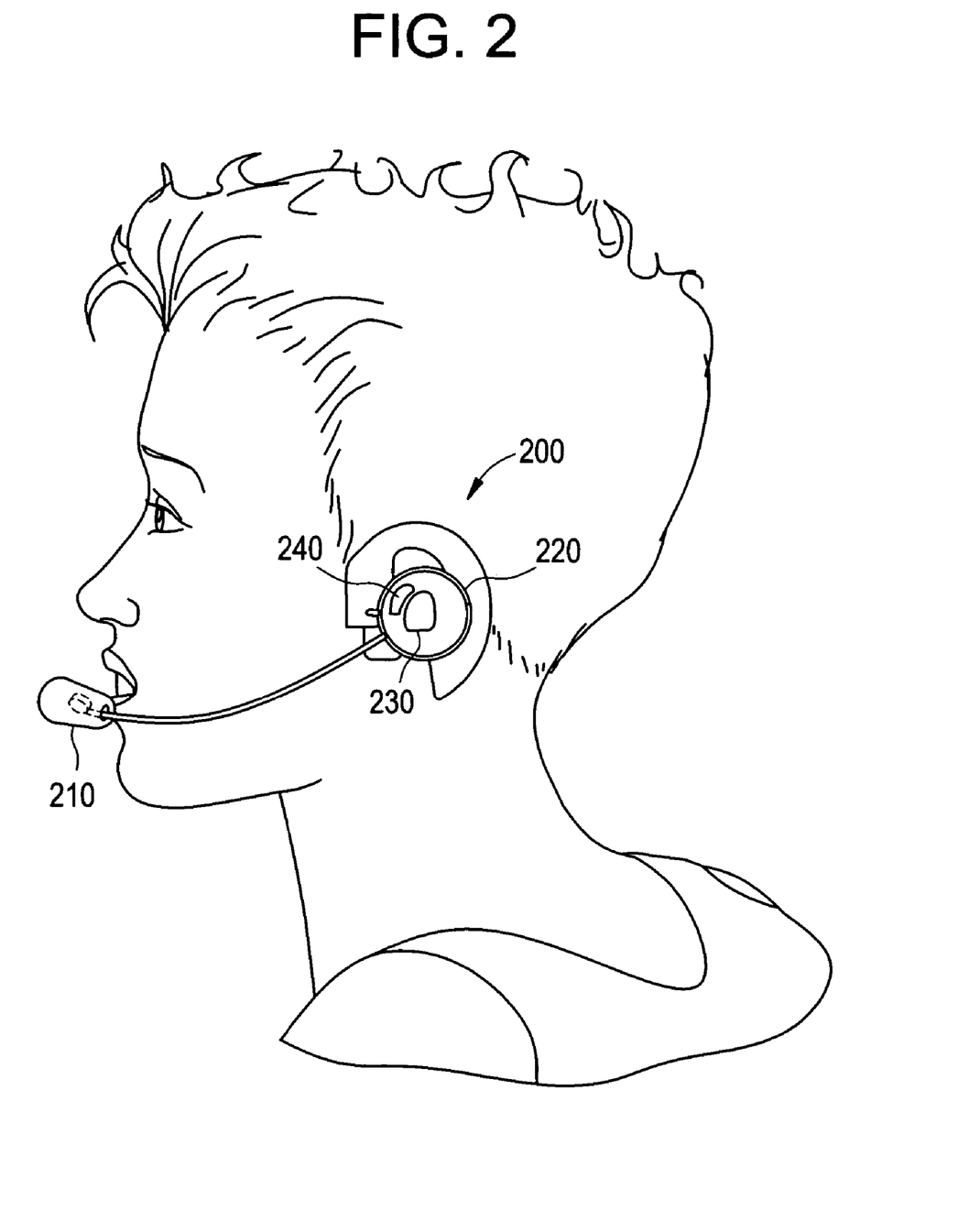
FIG. 2 illustrates an embodiment of a wireless headset used in accordance with an embodiment of the present invention.

The wireless communication device 110 may be implemented as a wireless headset. FIG. 2 illustrates an embodiment of a wireless headset 200 used in accordance with an embodiment of the present invention. The wireless headset 200 includes a microphone 210, an audio earpiece 220, speakers 230, and a wireless headset communication device 240. A person using the wireless headset 200 speaks into the microphone 210 and listens to audio sounds through the speakers 230 in the audio earpiece 220.

In operation, for example, a surgeon wears the wireless headset 200 within an operating room. The surgeon may request patient data, enter information about the current procedure, enter computer commands, and receive patient data using the wireless headset 200. To request patient data or enter computer commands, the surgeon speaks into the microphone 210. The request or command is transmitted from the wireless headset communication device 240 within the audio earpiece 220 of the wireless headset 200 to a local device via an interface device. The local device then executes command(s) received from the wireless headset communication device 240 within the wireless headset 200. If the surgeon requests patient information, the local device retrieves the information. The local device may then transmit the patient information to the wireless headset communication device 240 within the wireless headset 200 for playback through the speakers 230 in the audio earpiece 220 or the local device may transmit the patient information to another output device, such as the interface 120, for display or playback.

Before a medical procedure, for example, a surgeon may put on the wireless headset 200. The surgeon may then sterilize the surgeon's hands by scrubbing and putting on surgical gloves. After the medical procedure has begun, the surgeon may desire to view existing patient medical information stored in a storage device or enter new medical information obtained during the procedure. Rather than touch an unsterile computer keyboard or unsterile mouse, which would require re-sterilizing the surgeon's hands by re-scrubbing and re-gloving, the surgeon may use a more hygienic input devices such as the wireless headset 200, 110 and the interface 120.

By using the wireless headset 200, the surgeon's sterilized hands do not contact an unsterile surface such as the computer keyboard or computer mouse. The surgeon may speak requests and commands into the microphone 210 of the wireless headset 200. The wireless headset 200 then transmits the requests from the wireless headset communication device 240 to a local computer terminal. The local computer terminal processes the requests and commands from the wireless headset communication device 240 in the wireless headset 200.

Thus a user with the wireless communication device 110 may interact with a variety of electronic devices, such as the remote system 130, using the interface 120. As the user enters different rooms in a medical facility, the device 110 and/or the interface 120 synchronizes with one or more electronic devices or systems in a particular room. The user may then operate the device(s) using speech commands via the wireless communication device 110 and the interface 120. The user may also retrieve data from the device(s) using the device 110 and the interface 120.

In operation, a radiologist or other healthcare practitioner may wear and/or carry the device 110 and the interface 120 as he or she moves throughout a healthcare facility. Connections between the device 110, the interface 120 and other electronic systems in the facility may differ between different locations throughout the facility. For example, when a radiologist walks into an examination room, the wireless communication device 110 and the interface 120 establish a connection with a data collection device, such as a patient monitor, ECG machine, and/or an imaging system, for example. The wireless connection, for example, may be authenticated by a password, voice verification, electronic code or signature, or other biometric or security code.

For example, a radiologist wears a BLUETOOTH® wireless headset and carries a tablet PC. The radiologist enters a radiology reading room to review or enter image data. A computer in the room recognizes the wireless headset and tablet PC. That is, data is exchanged between the tablet PC and the computer to allow the tablet PC and the computer to synchronize. The radiologist is then able to access the computer via the tablet PC using voice commands at the headset. The radiologist may view, modify, and print images and reports using voice commands via the headset and tablet PC. The wireless headset and tablet PC enable the radiologist to eliminate excess clutter in a radiology workspace by replacing use of a telephone, keyboard, mouse, etc. with the wireless headset and tablet PC. The wireless headset and tablet PC or other similar device may simplify interaction with a plurality of devices and simplify a radiologist's workflow through use of a single interface point.

Figure 3:
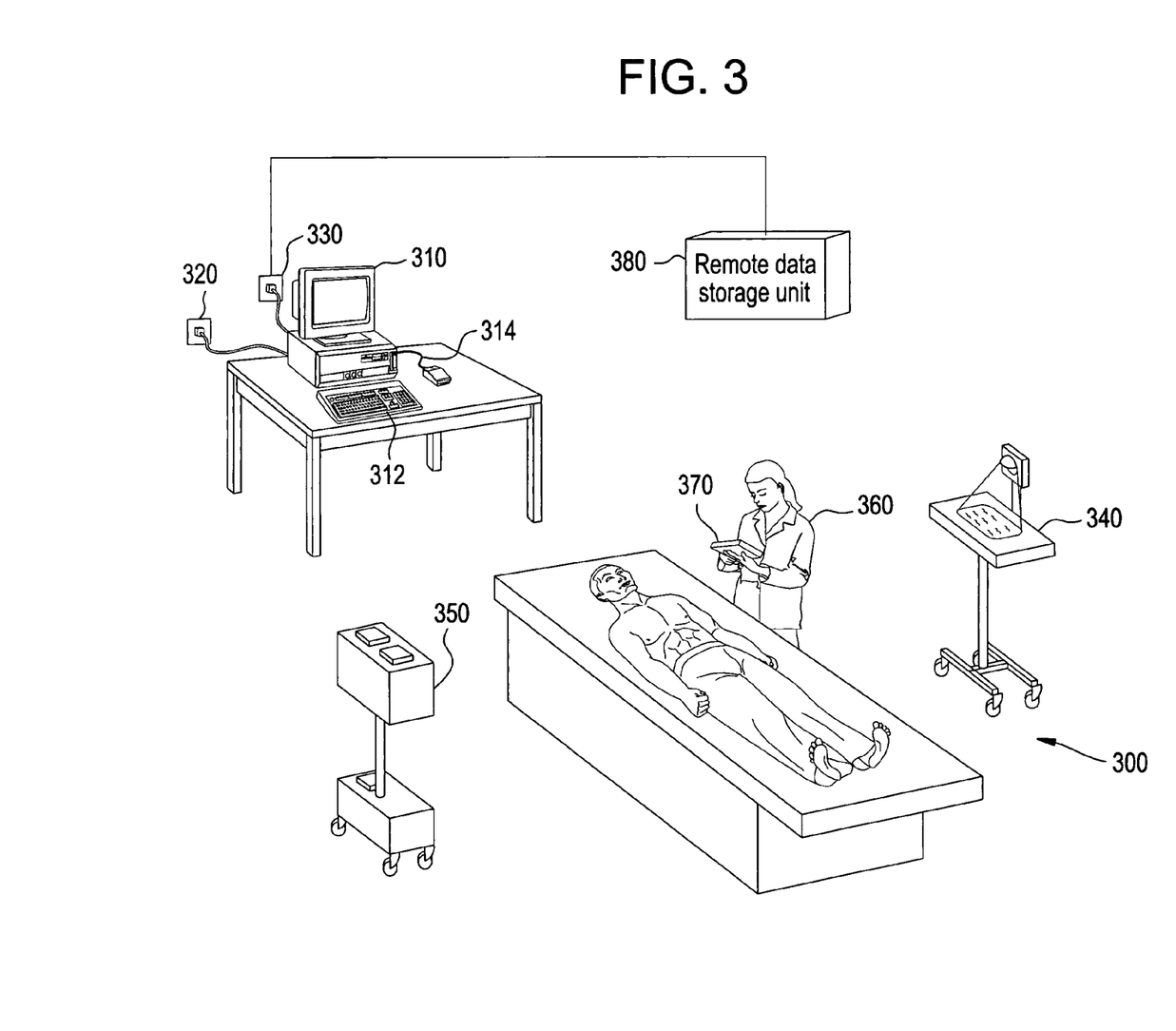
FIG. 3 depicts an example of a healthcare environment using wireless communication and control in accordance with an embodiment of the present invention.

FIG. 3 depicts an example of a healthcare environment 300 using wireless communication and control in accordance with an embodiment of the present invention. The environment 300 includes a local computer terminal 310, a hard-wired keyboard 312, a hard-wired mouse 314, a power outlet 320, a data port 330, a wireless input tray 340, a wireless interactive visual display system 350, a wireless headset 360, an interface device 370, and a remote data storage unit 380.

The remote data storage unit 380 stores patient medical information. The patient medical information may include medical data such as patient identifiers, images, lab results, medical diagnosis, and medical history. The remote data storage unit 380 transfers data to and from the local computer terminal 310 through the data port 330.

The local computer terminal 310 may be located within the environment 300, such as an operating room or in the vicinity of the operating room. The local computer terminal 310 is used by medical personnel to access the medical information stored in the remote data storage unit 380. The local computer terminal 310 plugs into and receives electrical power from the power outlet 320. The keyboard 312 and mouse 314 plug into local computer terminal 310. To access a patient's medical information and view medical data at the local computer terminal 310, medical personnel use their hands to manipulate the keyboard 312 and mouse 314 to control the local computer terminal 310. For example, information requests may be typed using the keyboard 312 or options may be selected on a screen by manipulating the mouse 314.

In addition to using the keyboard 312 or the mouse 314 to request patient medical information and enter new patient medical information, the wireless input tray 340, the wireless interactive visual display system 350, the wireless headset 360, and the interface 370 may be used. The wireless input tray 340, the wireless interactive visual display system 350, the wireless headset 360, and the interface 370 transfer data to and from the local computer terminal 310.

In operation, a surgeon may speak into the wireless headset 360 to request a patient's medical information. The wireless headset 360 transmits the surgeon's request to the local computer terminal 310. Communication between the wireless headset 360 and the local computer terminal 310 may use wireless communication standards such as the WiFi protocol or the BLUETOOTH® standard. Communication between the wireless headset 360 and the local computer terminal 310 may be facilitated by the interface 370. The local computer terminal 310 processes the request and accesses the remote data storage unit 380 to retrieve the requested data. After the requested data has been retrieved by the local computer terminal 310 from the remote data storage unit 380, the local computer terminal 310 transmits the requested data to an output device within the operating room.

In the healthcare environment 300 of FIG. 3, the wireless headset 360, the interface 370, and the wireless interactive visual display system 350 may be used as output devices. If the requested data includes audio data, the audio data may be transmitted to either of the wireless headset 360, the interface 370, and/or the wireless interactive visual display system 350 for audio playback. If the requested data includes video data, the video data may be transmitted to the wireless interactive visual display system 350 and/or the interface 370 for display.

The surgeon may also speak into the wireless headset 360 to add data to a patient's medical record or issue commands to the local computer terminal 310. The wireless headset 360 transmits the data or commands to the local computer terminal 310. The local computer terminal 310 then executes commands received from the wireless headset 360 and transmits data to the remote data storage unit 380 for storage with the patient's other medical information.

In certain embodiments, voice commands may be used to navigate through clinical applications such as a picture archiving and communication system (PACS), a radiology information system (RIS), a hospital information system (HIS), and an electronic medical record (EMR). A user's speech may be used to execute commands in a system, transmit data to be recorded at the system, and/or retrieve data, such as patient reports or images, from the system.

Additionally, in certain clean rooms, such as surgical suites and catheterization labs in a hospital or clinic, use of a keyboard or mousing device, such as a mouse, a trackball, or a touchpad, may be impractical or unsanitary. Voice command and control provide a flexible and sanitary alternative in an environment where a doctor may be unable to manipulate a manual interface. Furthermore, voice command and control may be used to avoid or compensate for repetitive stress injuries due to manual access devices.

In certain embodiments, spoken words may be converted to text for storage and/or display at a remote system 130. Additionally, text at the remote system 130 may be converted to audio for playback to a user via the wireless communication device 110. For example, a radiologist or other healthcare practitioner may dictate reports without holding a microphone or other recording device. Using BLUETOOTH® wireless technology, for example, dictation may be facilitated using voice recognition software on the interface 120 or the remote system 130. Alternatively, voice commands may be used to dial a telephony transcription service for remote dictation. Translation software allows dictation as well as playback of reports, lab data, examination notes, and image notes through the wireless communication device 110. Audio data may be review in real-time in stereo sound via the device 110. For example, a digital sound file of a patient heartbeat may be reviewed by a physician remotely through a BLUETOOTH® headset.

The wireless communication device 110 and interface 120 may also be used to communicate with other medical personnel in a facility. For example, a user may page another practitioner for a consultation using the wireless communication system 100. Alternatively, the wireless communication system 100 may be used to telephone another practitioner. Thus, the user may be away from a phone and still communicate with others inside or outside the medical facility. In an embodiment, the wireless communication system 100 allows a healthcare practitioner to check voice-mail messages or other communications remotely.

Certain embodiments may improve reporting by healthcare practitioners and allow immediate updating and revising of reports using voice commands. Clinicians may order follow-up studies at a patient's bedside or during rounds without having to locate a mouse or keyboard. Additionally, reports may be signed verbally, eliminating delay or inconvenience associated with a written signature.

The wireless communication system 100 may also be used with voice over Internet protocol (IP) to transmit voice audio data. For example, a specialist may call a referring doctor without picking up a phone. A radiologist may consult a colleague without paging the colleague. Additionally, voice over IP may be used to order additional images or tests.

Certain embodiments provide voice authentication to access clinical systems. The wireless communication device 110 working with the interface 120 may access the remote system 130 using voice commands. A user's voice print, a password, or a combination of voice and password authentication, for example, may be used to authenticate the user for access to the remote system 130. Verbal authentication may provide improved and more efficient system security over traditional typed password entry.

Figure 4:
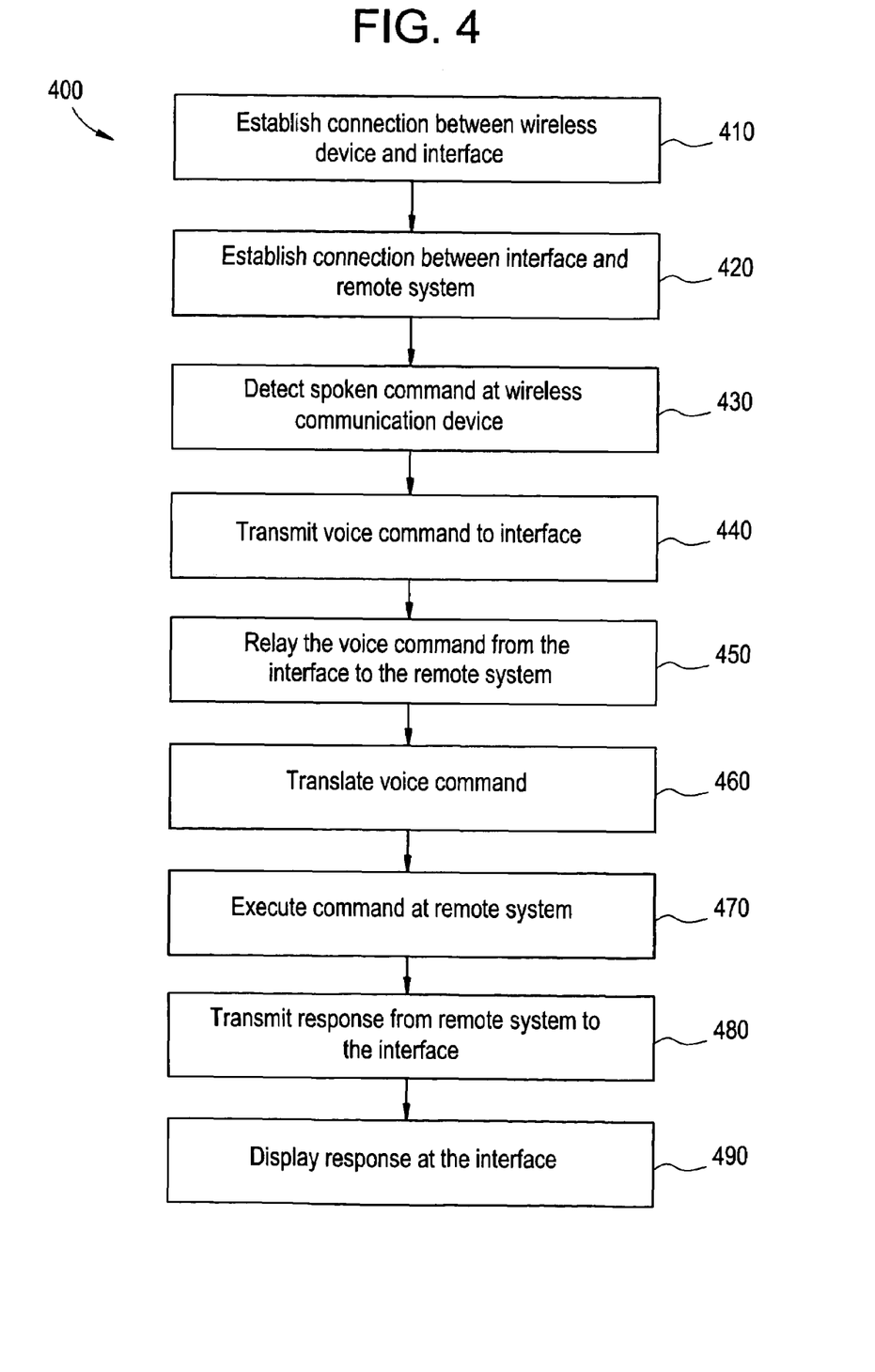
FIG. 4 shows a flow diagram for a method for wireless voice communication in a clinical workflow in accordance with an embodiment of the present invention.

FIG. 4 shows a flow diagram for a method 400 for wireless voice communication in a clinical workflow used in accordance with an embodiment of the present invention. First, at step 410, a connection is established between the wireless communication device 110 and the interface 120. Data packets are transmitted between the wireless device 110 and the interface 120 to establish a communication link between the device 110 and the interface 120. The communication link may also be authenticated using voice identification or a password, for example.

Then, at step 420, a connection is established between the interface 120 and the remote system 130. Data packets are transmitted between the interface 120 and the remote system 130 to establish a communication link between the interface 120 and the remote system 130. The communication link may also be authenticated using voice identification or a password, for example. After the communication links have been established, a user may communicate with the remote system 130 via the wireless communication device 110 and the interface 120.

Next, at step 430, a user speaks a command that is detected by the wireless communication device 110. At step 440, the voice command is transmitted to the interface 120. Then, at step 450, The interface 120 relays the voice command to the remote system 130. At step 460, the received voice command is translated by the remote system 130. Software running at the remote system 130 translates the spoken command to a command executable by the remote system 130.

Then, at step 470, the command is executed by the remote system 130. For example, a program may be executed at the remote system 130 in response to the voice command. Alternatively, for example, data may be retrieved at the remote system 130 in response to the voice command. A test or image acquisition, for example, may be initiated at the remote system 130 in response to the voice command. In another embodiment, a plurality of voice commands may be transmitted to the remote system 130 and executed.

Next, at step 480, a response is transmitted from the remote system 130 to the interface 120. For example, an acknowledgement of an action may be transmitted to the interface 120. Alternatively, for example, data retrieved at the remote system 130 may be transmitted to the interface 120. At step 490, the response may be displayed at the interface 120. A user may view the results at the interface 120. Alternatively, the interface 120 may relay the response to the wireless communication device 110 for audio broadcast to the user.

The wireless communication device 110 and the interface 120 may be used to communicate with a variety of remote systems and devices. For example, the device 110 and the interface 120 may control and retrieve data from an imaging system, a computer, an image or data storage system (such as a PACS), a telephone system, an electronic mail system, a surgical navigation system, and/or other electronic system in a healthcare facility. In an embodiment, the wireless communication device 110 may communicate directly with the remote system 130. Alternatively, the interface 120 may be integrated with the wireless communication device 110.

Thus, certain embodiments provide an improved or simplified workflow for a clinical environment, such as radiology. Certain embodiments allow a user to operate a single interface device with wireless communication to access functionality and transfer data in any given environment in a healthcare facility. Certain embodiments provide a system and method for a user to consolidate the workflow of all devices in an environment, such as a desktop or operating room, into one wireless, voice-enabled, digital workflow. Certain embodiments provide a system and method for a user to activate and perform wireless voice authentication. Certain embodiments provide a system and method for wireless voice data entry, such as wireless voice order entry and confirmation, wireless digital voice dictation, and wireless voice signature. Certain embodiments provide wireless voice control, such as wireless voice control of clinical application software, wireless clinical review of audio data, and wireless voice over IP conferencing.

Certain embodiments of the present invention provide increased efficient and throughput for medical personnel, such as radiologists and physicians. The system and method reduce desktop and operating room clutter, for example. Certain embodiments provide increased security for clinical applications and data through biometric authentication. Repetitive motion injuries may also be reduced or eliminated.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A wireless communication system for facilitating clinical workflow, said system comprising:
   a remote system in a healthcare facility, said remote system used for at least one of executing an operation, storing data, and retrieving data;
   a wireless communication device for voice control of said remote system in said healthcare facility, said wireless communication device adapted for centralized control of said remote system to facilitate at least one of executing an operation, storing data, and retrieving data at said remote system based on a voice command issued via said wireless communication device; and
   an interface for relaying communication between said remote system and said wireless communication device, said interface displaying data from said remote system.

2. The system of claim 1, further comprising a plurality of remote systems, said plurality of remote systems capable of communicating with said wireless communication device.

3. The system of claim 1, wherein said interface displays data from said wireless communication device.

4. The system of claim 1, wherein said wireless communication device produces an audio response from said remote system.

5. The system of claim 1, wherein said wireless communication device is a wireless communication device configured according to a standard for voice and data transfer between devices without use of cables.

6. The system of claim 1, wherein said wireless communication device is a wireless headset.

7. The system of claim 1, wherein said interface is integrated with said wireless communication device.

8. The system of claim 1, wherein said wireless communication device communicates directly with said remote system.

9. The system of claim 1, wherein said wireless communication device and said interface control said remote system to perform at least one of data acquisition, data retrieval, order entry, dictation, audio playback, voice over IP conferencing, paging, and data analysis.

10. A method for facilitating workflow in a clinical environment, said method comprising:
    establishing a communication link between a wireless, voice-enabled communication device and a remote system at a first location using an interface;
    detecting a voice command spoken at said wireless, voice-enabled communication device;
    transmitting said voice command to said interface;
    relaying said voice command from said interface to said remote system; and
    utilizing voice commands from said wireless, voice-enabled communication device to at least one of transmit data to, retrieve data from, and trigger functions at said remote system via said communication link.

11. The method of claim 10, further comprising receiving a response from said remote system.

12. The method of claim 10, further comprising establishing a second communication link between said wireless communication device and a second remote system at a second location.

13. The method of claim 10, further comprising establishing a plurality of communication links between said wireless communication device and a plurality of remote systems at said first location.

14. The method of claim 10, further comprising performing authentication for said communication link.

15. The method of claim 10, further comprising using voice commands to perform at least one of data acquisition, data retrieval, order entry, dictation, audio playback, voice over IP conferencing, paging, and data analysis.

16. A method for consolidating workflow of a plurality of devices into a wireless, voice-enabled workflow, said method comprising:
    establishing a connection between a wireless, voice-enabled device and a data system using an interface;
    detecting a voice command spoken at said wireless communication device;
    transmitting said voice command to said interface;
    relaying said voice command from said interface to said data system; and
    accessing said data system using said voice command via said connection between said wireless communication device and said data system facilitated by said interface.

17. The method of claim 16, wherein said accessing step further comprises using voice commands to facilitate at least one of data acquisition, data retrieval, order entry, dictation, audio playback, voice over IP conferencing, paging, and data analysis.

18. The method of claim 16, further comprising establishing a plurality of connections between said wireless, voice-enabled device and a plurality of data systems.

19. The method of claim 16, further comprising using WiFi wireless technology or other standard for voice and data transfer between devices without use of cables to facilitate hands-free hygienic, centralized operation of a plurality of data systems using said wireless, voice-enabled device and said interface.

* * * * *